United States Patent [19]

Foá et al.

[11] Patent Number: 5,352,830
[45] Date of Patent: Oct. 4, 1994

[54] PHOSPHOROUS ORGANIC AMIDES SUITABLE AS STABILIZERS AND POLYMER COMPOSITIONS WHICH COMPRISE THEM

[75] Inventors: Marco Foá; Sauro Strologo, both of Novara; Giampiero Sabarino, Vercelli, all of Italy

[73] Assignee: Himont Incorporated, Wilmington, Del.

[21] Appl. No.: 967,892

[22] Filed: Oct. 28, 1992

[30] Foreign Application Priority Data

Oct. 31, 1991 [IT] Italy ............... MI91 A 002909
Oct. 31, 1991 [IT] Italy ............... MI91 A 002908

[51] Int. Cl.$^5$ ............................................. C07F 9/02
[52] U.S. Cl. ................................. 564/12; 524/117; 524/119
[58] Field of Search .................. 564/12, 14, 13, 16; 544/157; 524/117, 119

[56] References Cited

U.S. PATENT DOCUMENTS 4,055,539 10/1977 Rosenberger ............... 260/45.95
4,259,429  3/1981 Gilliams et al. ............ 430/134
4,322,527  3/1982 Rasberger ................... 544/157

FOREIGN PATENT DOCUMENTS 0108714  6/1984 European Pat. Off. .

OTHER PUBLICATIONS

CA 98(11): 89664, 1982 Abstract only.
CA 114: 187328, 1991 Abstract only.
Makmeneva et al., Zh. Obschch. Khim. vol. 56, No. 10, pp. 2267–2271 (2001–2004 of Eng translation), 1986.

*Primary Examiner*—Shailendra Kumar

[57] ABSTRACT

New phosphorous organic amides of a specific formula and their use as stabilizers for polymers and, other organic materials.

4 Claims, No Drawings

PHOSPHOROUS ORGANIC AMIDES SUITABLE AS STABILIZERS AND POLYMER COMPOSITIONS WHICH COMPRISE THEM

The invention relates to a class of phosphorous organic amids compounds suitable as stabilizers for organic materials, polymers in particular, and polymer compositions comprising them.

It is well known that polymer substances such as for example the polyolefins, show a tendency to rapidly degrade when exposed to air, or to oxidizing agents in general, and to light. Said degradation, which causes a deterioration of their physical characteristics, is increased by the heat treatments to which polymers are subjected during manufacturing.

Stabilizers are used to counteract said degradation, but none of them by themselves possess adequate properties for complete protection of the polymer from oxidizing agents, light, and heat treatments, therefore mixtures of stabilizers offering specific functions are used such as antioxidants, U.V. stabilizers, U.V. radiation absorber. Typically these mixtures comprise an oxygenated organic compound of phosphorous, particularly a phosphite, a phosphonite, or a phosphorous amide. The particular action of the above mentioned phosphoric compounds may be summarized as follows:

1) they hinder the molecular weight alteration which occurs during polymer processing;
2) reduce the coloration of the polymer following heat treatments; and
3) have a secondary antioxidating effect, preventing the onset of radical phenomena is the basis of the degradation processes.

Some classes of organic phosphites and phosphenites are widely used in the polymer stabilization field.

In particular, a compound representing the phosphites used as stabilizers, is IRGAFOS 168 tri(2,4-di-tert-butylphenyl) phosphite.

One widely used phosphonite is SANDOSTAB P-EPQ tetrakis (2,4-di-tert-butyl-phenyl) 4,4′-diphenyl diphosphonite.

Some classes of phosphoric organic amides are also known.

For example, U.S. Pat. No. 4,259,492 refers to dioxaphosphepines of formula:

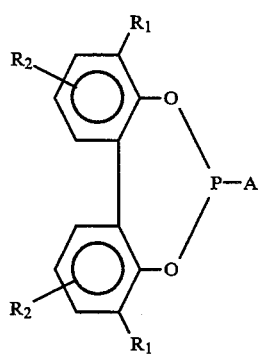

where:
$R_1$ is a $C_1$-$C_8$ alkyl radical, $R_2$ is H or a $C_1$-$C_{18}$ alkyl radical, and A is a group derived from a primary or secondary amine having the same or different radicals which can be aliphatic, alicyclic, aromatic or arylalkyl, or A is a group derived from a heterocyclic amine, or a hydrazine compound.

In U.S. Pat. No. 4,322,527 are described particular dibenzo[1,3,2]dioxaphosphocines of formula:

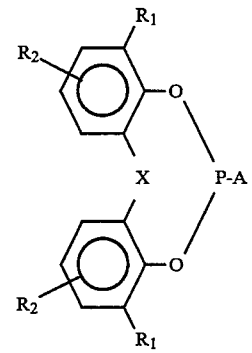

where:
$R_1$ is selected from H, a $C_1$-$C_{18}$ alkyl, a $C_5$-$C_{12}$ cycloalkyl, a $C_7$-$C_9$ phenyl or phenylalkyl radical, $R_2$ can be H, or a $C_1$-$C_{18}$ alkyl radical, X is S or a —$CHR_3$ group, where $R_3$ is H, or a radical of formula —$CHR_4$—$CHR_5SR_6$, where $R_4$ and $R_5$ are independently H, or a $C_1$-$C_6$ alkyl radical, and $R_6$ is a $C_1$-$C_{20}$ alkyl radical, and A is a primary or secondary aliphatic, alicyclic, aromatic or araliphatic amine containing substituents of the same type or different, or is a derivative of a heterocyclic amine or a hydrazine compound.

In European patent application EP-A-O 108 714, are described dibenzo-dioxaphosphepines and/or dibenzo-dioxaphosphocines derived from alkanolamines and having the general formula:

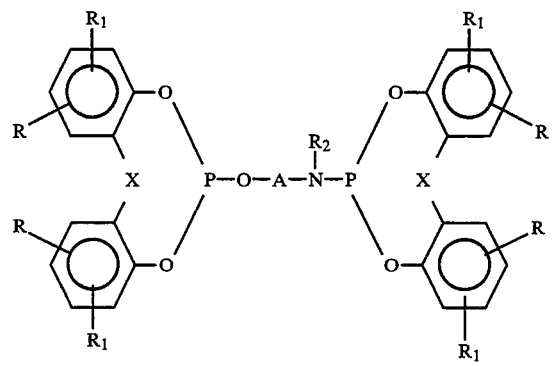

where:
R and $R_1$ are the same or different and are H, or a $C_1$-$C_{18}$ alkyl, $C_5$-$C_{12}$ cycloalkyl, $C_7$-$C_{24}$ phenyl or phenylalkyl radical, $R_2$ is H, or a $C_1$-$C_{12}$ alkyl or a phenyl radical, A is a $C_1$-$C_6$ alkylene or $C_5$-$C_6$ cycloalkylene radical, and X is a single bond or a $C_1$-$C_{12}$ alkylidene radical.

One disadvantage generally associated with the use of phosphoric compounds in the stabilization of polymers is that many of them present a certain hygroscopicity, and poor resistance to hydrolysis. This involves, for example, the use of some necessary precautions during the storage of polymers additivated with said compounds, in order to reduce or eliminate the absorption of water by the polymer, and the hydrolysis of the phosphorated compound.

Therefore, the purpose of this invention is to supply a new class of compounds containing phosphorous, in particular phosphorous amides, that combine excellent stabilizing properties with an improved resistance to hydrolysis and water absorption as compared to the phosphoric compounds known up to now and normally used in the industry for the stablization of polymers.

In particular, the compounds of the present invention are phosphorous organic amides, having the general formula:

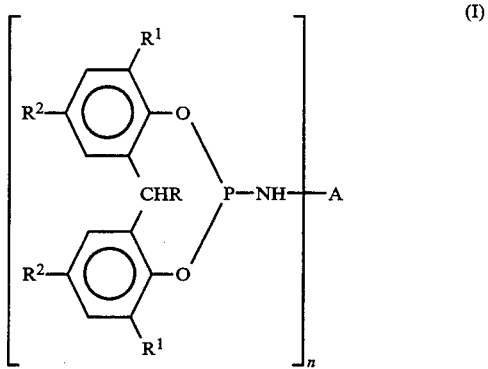

where:
R is H or a $C_1$–$C_{18}$ radical,
$R^1$ and $R^2$ are the same or different, and are selected from $C_1$–$C_{10}$ linear or branched alkyl radicals,
n is 1 or 2, and
A, when n is 1, is a radical of formula —$(CH_2)_m$—Cy, where Cy is a mono- or polycyclic $C_5$–$C_{20}$ aliphatic radical, optionally substituted with alkyl or alkoxy groups, and m is 0 or 1;
when n is 2, A is selected from a $C_2$–$C_{20}$ alkylene, 4 $C_{20}$ alkenylene, $C_5$–$C_9$ alkinylene, $C_5$–$C_8$ cycloalkylene, or a

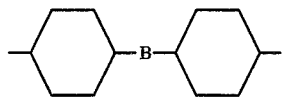

group, where B is selected from O, S, a phenylene or bis-phenylene radical, or a >$CR^3R^4$ group, where $R^3$ and $R^4$ are selected from H or a $C_1$–$C_8$ alkyl radical, or they can form a $C_5$–$C_{12}$ ring with the carbon to which they are bonded.

The Applicants have unexpectedly found that by selecting the proper A radical bonded to the nitrogen in formula (I), it is possible to obtain compounds that, besides being particularly adequate as polymer stabilizers, are very slightly hygroscopic and hydrolyzable, as previously stated.

Preferably, R is H or a $C_1$–$C_{11}$ alkyl radical, $R^1$ and $R^2$ are preferably: tert-butyl, isopropyl, methyl, and most preferably at least one of the two is a tert-butyl.

When n is 1, A is preferably selected from the group consisting of: abietyl, hydroabietyl, tetrahydroabietyl, dehydroabietyl, d- and l-pimaryl and cyclohexyl. Radicals like the abietyl present the further advantage of rendering the stabilizing molecule more compatible with the polymer matrix to be stabilized, thus considerably preventing the "blooming" phenomenon, i.e., the migration of the stabilizer to the surface of the polymer products, which results in loss of the stabilizer itself and decreased the aesthetic characteristics of the products.

When n is 2, A is preferably selected from: ethylene, hexamethylene, and 4,4'-alkylidene-bis-cyclohexyl radicals.

Examples of the compounds of formula (I) are: 2,2'-methylene -bis-(2,4-di-tert-butyl-phenyl)-N-cyclohexylphosphorous amide, 2,2'-ethylidene-bis(2,4-di-tert-butylphenyl) -N-dehydroabietyl-phosphorous amide, 2,2'-ethylidene-bis(2,4-di-tert-butylphenyl)-N-cyclohexylphosphorous amide, N,N'-bis[2,2'-ethylidene-bis(2,4-di-tert -butylphenyl)phosphorous]-1,6-hexanediamide, 2,2' -butylidene-bis(2,4-di-tert-butylphenyl)-N-dehydroabietyl-phosphorous amide, 2,2'-hexylidene-bis(2,4-di-tert-butylphenyl) -N-dehydroabietyl-phosphorous amide, 2,2'-dodecylidene-bis (2,4-di-tert-butylphenyl)-N-dehydroabietylphosphorous amide, 2,2'-dodecylidene-bis(2,4-di-tert-butylphenyl) -N-cyclohexyl-phosphorous amide, 2,2'butylidene -bis(2,4-di-tert-butylphenyl)-N-cyclohexyl phosphorous amide, and 2,2'-hexylidene-bis (2,4-di-tert-butylphenyl) -N-cyclohexyl-phosphorous amide.

The compounds of formula (I) are also slightly volatile, and this will keep them from dissipating during the processing phase of the polymer to which they are added.

Moreover, by adequately selecting the $R^1$, $R^2$, and A radicals, it is possible to obtain compounds having a melt point higher than 200° C.

The compounds of formula (I) can be obtained starting from his-phenols of formula (II)

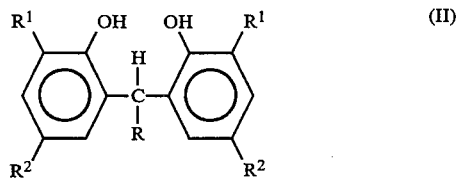

The compounds of formula (II) are commercially available, or can be prepared starting from phenols of formula (IV), according to the following reaction:

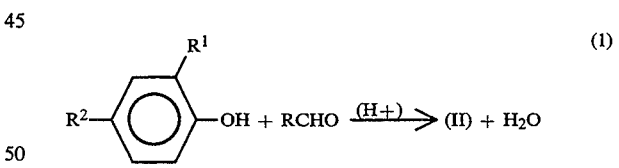

Said reaction is described, for example, in "Beaver, D.J. and Stoffel, P.J., "Journal of the American Chemical Society, 74, 3410, (1952)".

The bis-phenols of formula (II) are caused to react with $PCl_3$ to produce the compounds of formula (III)

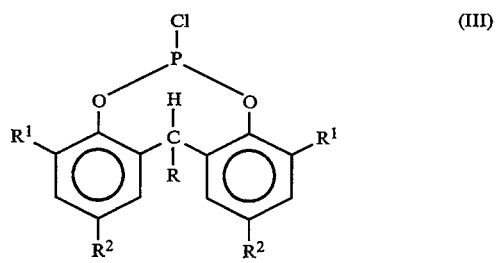

according to the following reaction:

$$(II) + PCl_3 + 2B' \rightarrow (III) + 2B'.HCl \qquad (2)$$

In said reaction, B' represents an organic or inorganic basic compound. Preferred B' compounds are the tertiary amines, such as triethylamine, pyridine bases, and ammonia.

Reaction (2) is preferably carried out in a solvent medium. Preferred solvents are the aromatic hydrocarbons, such as benzene, toluene, and xylene. Aliphatic and cycloaliphatic hydrocarbons, such as ligroin and petroleum ether, organic chlorinated compounds, such as chloroform Dr 1,2-dichloroethane, and the ethers, such as ethyl ether or diglyme, can also be used as solvents.

Reaction (2) occurs at a temperature comprised between 0° C. and the boiling temperature of the solvent used.

Intermediate (III) can be separated from the reaction mixture, after filtration of the B'eHCl, by evaporating the solvent, and is used without needing further purification.

As an alternative, the solution of intermediate (III), or its suspension, can be used as starting material for the preparation of compounds (I).

In order to prepare compounds (I), intermediate (III) is reacted with an amine as shown in the following reaction:

$$n(III) + (H_2N)_nA + nB'' \rightarrow (I) + nB''.HCl \qquad (3)$$

where B'' is a basic compound that is the same or different from B', but having the same meaning as B'.

Reaction (3) also occurs preferably in a solvent medium having the same characteristics as the one described above for reaction (2). In this case, however, one preferably uses those solvents where the compounds of formula (I) are soluble and the B''.HCl salts insoluble at room temperature.

The reagents are used preferably in stoichiometric quantities, while base B'' is preferably used in excess of about 10% with respect to the stoichiometric quantity.

The compounds of formula (I) are separated from the reaction mixture, after the B''.HCl salt has been filtered, by evaporating the solvent. They can then be purified, for example, by recrystallization.

In order to confer process stability to the polymers only small quantities of the compounds object of the present invention are sufficient.

The quantity of said compounds which can be adequately used to obtain stabilization is generally from 0.01 to 3 parts by weight for 100 parts by weight of the material to be stabilized.

In particular, object of the present invention are also the polymer compositions comprising the compounds of formula (I) in quantities from 0.01 to 3 parts by weight per i00 parts by weight of the polymer material to be stabilized.

The compounds of formula (I) are effective as stabilizers in synthetic and natural polymers, as well as in other organic materials, such as mineral, vegetable or animal oils, and mixtures thereof.

The polymers in which the compounds of formula (I) have shown to be particularly effective as stabilizers comprise: polymers and copolymers, or blends thereof obtained by sequential polymerization, of the olefins of formula R'''—CH=CH$_2$, where R''' is a hydrogen atom, or a 1-6 carbon alkyl or an aryl radical.

In particular, said polymers and copolymers comprise:

i) isotactic or mainly isotactic polypropylene;
ii) HDPE, LLDPE, and LDPE polyethylene
iii) crystalline copolymers of propylene with ethylene and/or other α-olefins, such as for example 1-butene, 1-hexene, 1-octene, and 4-methyl-1-pentene;
iv) ethylene/α-olefin elastomeric copolymers, and ethylene/α-olefin/diene terpolymers containing minor proportions of diene, where the α-olefin is preferably selected from propylene, 1-butene, 1-pentene, 1-hexene, 4-methyl-1-pentene, and 3-methyl-1-butene (examples of dienes most commonly present in the above mentioned elastomeric copolymers are butadiene, ethylidenenorbornene, and 1-4 hexadiene;
v) heterophasic polymers obtained by sequential polymerization, made up of (A) a homopolymer fraction of propylene, or one of the copolymers listed above in (iii), and a copolymer fraction (B) formed by the elastomeric copolymers listed above in (iv).

The stabilizers of the present invention can easily be incorporated in the polymers by way of conventional techniques at any stage of the process which precedes the forming of the manufactured article. The stabilizer can be mixed with the polymer by using various techniques, such as dry-blending in powder form, or wet-blending in the form of solutions, suspensions, or even in the form of masterbatch. In said operations the polymer can be used in powder, pellets, solution, suspension, or latex form.

The compounds of the present invention can be used together with other conventional additives for polymers, such as antioxidants, light stabilizers and UV absorbers, NI based stabilizers, pigments, reinforcing agents, plasticizers, antiacids, antistatic agents, flame retardants, lubricants, corrosion inhibitors, metal complexing agents, scavengers of peroxides, other basic co-stabilizers, and nucleating agents.

The following examples are given to illustrate and not limit the present invention.

All percentages are calculated by weight.

EXAMPLE A

Preparation of 2,2'-ethyltdenebis(2,4-di-tert-butylphenyl)phosphorous chloride

Into a 1 liter three-neck flask equipped with a refrigeration device and a mechanical agitator, are introduced, in nitrogen atmosphere, in order: 200 ml anhydrous toluene and 13.75 g (100 mmoles) of PCl$_3$. The solution is agitated and cooled in an ice bath, until it reaches a temperature of 0°-5° C. To this solution are added. dropwise, over a period of thirty minutes, a solution of 43.8 g (100 moles) of 2,2'-ethylidene-bis-(2,4-di-tert -butyl)phenol, and 20 ml (200 mmoles) of triethylamine, in 200 ml of toluene.

At the end of the addition the resultant mixture is allowed to reach ambient temperature, the agitation is discontinued, and the mixture is heated to 50° C. for 8 hrs.

Subsequently, the suspension thus obtained is cooled to ambient temperature and filtered in inert atmosphere.

The solid collected on the filter is washed twice with 50 ml of toluene.

The filtrate and wash solvent are combined and the solution is evaporated at reduced pressure, and the solid obtained is dried under vacuum. Thus 47.1 g (93.5% yield) of the desired product are obtained; its structure is confirmed by way of mass spectrometry and elemental analysis: C% 72.02 (theoretical 71.62); H% 8.93 (theoretical 8.82); Cl% 6.93 (theoretical 7.05); P% 5.51 (theoretical 6.16). The molecular weight, determined by way of mass spectrometry, is (MH)+ =503 (where (MH)+ represents the molecular weight of the substance plus a protone).

EXAMPLE 1

Preparation of 2,2'-methylene-bis-(2,4-di-tert-butylpheny)-N-cyclohexyl-phosphorous amide Into a 250 ml double neck flask, equipped with a refrigerating device, in nitrogen atmosphere, are introduced in order: 100 ml of anhydrous toluene, 2 ml (14 moles) of triethylamine, 1.5 ml (13 moles) of cyclohexylamine, and 5.56 g (13 mmoles) of 2,2'-methylene-bis-(2,4-di-tert-butylphenyl)chlorophosphite, prepared according to the method described in Example A, except using 2,2'-methylene-bis(2,4-di-tert-butyl)phenol as starting material instead of 2,2'-ethylidene-bis-2,4-di-tert-butyl)phenol.

The solution is maintained while agitating with a magnetic agitator at a temperature of 80° C. for 12 hrs. The suspension obtained is cooled to ambient temperature and filtered, then the solid gathered on the filter is washed twice with 20 ml of toluene. The filtrate and the wash solvent are combined and the solution obtained is evaporated. at reduced pressure. The solid obtained from the evaporation of the solution is then washed with 100 ml of petroleum ether, and dried under vacuum.

6.2 g (84% yield) of the desired product are obtained with the following elemental analysis:

C% 76.20 (theoretical 76.15); H% 9.97 (theoretical 9.86);

N% 2.63 (theoretical 2.53); P% 5.31 (theoretical 5.61).

The structure of the compound obtained has been confirmed by mass spectrometry, which also determined the molecular weight of the compound, (MH)+ =552.

EXAMPLE 2

Preparation of 2,2'-ethylidene-bis-(2,4-di-tert-butylphenyl)-N-dehydroabietyl-phosphorous amide Into a 500 ml double-neck flask, equipped with a refrigerating device, are introduced, in nitrogen atmosphere, in order: 200 ml of anhydrous toluene, 9.6 g (30 mmoles at 90%) of dehydroabietyl amine, 4.2 ml (30 mmoles) of triethylamine, and 15.1 g (30 mmoles) of 2,2'-ethylidene-bis(2,4-di-tert-butylphenyl)phosphorous chloride prepared in example A.

The resulting solution is maintained under agitation with a magnetic agitator, and the temperature is maintained at 80° C. for 12 hours. The suspension obtained is cooled to ambient temperature and filtered, and the solid collected on the filter is washed twice with 20 ml of toluene. The filtrate and wash solvent are combined, and the solution obtained is evaporated at reduced pressure. The solid obtained from the evaporation of the solution is then washed with 100 ml of petroleum ether, and then dried under vacuum. Thus one obtains 15.8 g (70% yield) of the desired product are obtained.

The results of the elemental analysis of said product are as follows:

C% 79.55 (theoretical 79.84); H% 9.81 (theoretical 9.92);

N% 1.74 (theoretical 1.86); P% 3.45 (theoretical 4.12).

The structure of the compound obtained has been confirmed by way of mass spectometry, which was used also to determine the molecular weight of the compound: (MH)+ =752.

EXAMPLE 3

Preparation of 2,2'-ethylidene-bis-(2,4-di-tert-butylphenyl)-N-cyclohexyl-phosphorous amide Into a 250 ml double neck flask, equipped with a refrigerating device, in nitrogen atmosphere, are introduced in order: 100 ml of anhydrous toluene, 2 ml (14 mmoles) of triethylamine, 1.5 ml (13 mmoles) of cyclohexylamine, and 6.47 g (13 mmoles) of the phosphorous chloride prepared as described in Example A.

Using the same operating methods described in Example 1, 5.5 g (75% yield) of the desired product are obtained with the following elemental analysis:

C% 76.90 (theoretical 76.42); H% 10.01 (theoretical 9.98);

N% 2.29 (theoretical 2.47); P% 4.28 (theoretical 5.48).

The structure of the compound obtained has been confirmed by mass spectrometry, which was also used to determine the molecular weight of the compound: (MH)+ =566.

COMPARATIVE EXAMPLE 1

Preparation of 2,2'-ethylidene-bis-(2,4-di-tertbutylphenyl)-N-dodecyl-phosphorous amide Into a 250 ml double neck flask, equipped with a refrigerating device, in nitrogen atmosphere, are introduced in order: 100 ml of anhydrous toluene, 1.09 g (11.34 mmoles) of dodecylamine, 2.1 ml (15 mmoles) of triethylamine, and 5.7 g (11.3 mmoles) of the phosphoric chloride prepared as described in Example A.

Operating as described in Example 1, 6.54 g (88% yield) of the desired product are obtained. The elemental analysis of said product is as follows:

C% 76.90 (theoretical 77.37); H% 11.03 (theoretical 10.82);

N% 2.24 (theoretical 2.15); P% 4.58 (theoretical 4.75).

The structure of the compound obtained was confirmed by mass spectrometry, which was also used in the determination of the molecular weight of the compound: (MH)+ =652.

COMPARATIVE EXAMPLE 2

Preparation of 2,2'-ethylidene-bis-(2,4-di-tert-butylphenyl)-N-octadecyl,phosphorous amide Into a 250 ml double neck flask, equipped with a refrigerating device, in nitrogen atmosphere, are introduced in order: 100 ml of anhydrous toluene, 5.36 g (20.2 mmoles) of octadecylamine, 5 g (9.95 mmoles) of the phosphoric chloride prepared as described in Example A.

Operating as described in Example 1, 6.4 g (87% field) of the desired product are obtained. The elemental analysis of said product is as follows:

C% 77.15 (theoretical 78.36); H% 11.2 (theoretical 11.15);

N% 1.62 (theoretical 1.90); P% 3.77 (theoretical 4.21).

The structure of the compound obtained was confirmed by way of mass spectrometry, which are also used in the determination of the molecular weight of the compound: (MH)+ = 736.

EXAMPLE 4

Preparation of N,N'-bis[2,2'-ethylidene-bis(2,4-di-tert-butylphenyl)phosphorous]-1,6-hexanediamide Into a 250 ml double neck flask, equipped with a refrigerating device, in nitrogen atmosphere, are introduced in order: 60 ml of toluene and 5 g (10 mmoles) of the phosphorous chloride prepared as described in Example A. The solution is maintained under agitation, and adds 0.577 g (5 mmoles) of 1,6-diaminohexane dissolved in 20 ml of toluene are added.

The solution is maintained under agitation by way of a magnetic agitator for a period of 12 hours at a temperature of 80° C. The suspension obtained is cooled to ambient temperature and filtered, and the solid collected on the filter is washed twice with 20 ml of toluene. The filtrate and wash solvent are combined and the solution obtained is evaporated at reduced pressure. The solid obtained from the evaporation of the solution is then washed with 100 ml of ethyl ether, and finally dried under vacuum.

3.9 g (74% yield) of the desired product are obtained. The elemental analysis of said product is as follows:

C% 75.16 (theoretical 75.57); H% 9.91 (theoretical 9.80);

N% 2.59 (theoretical 2.67); P% 5.09 (theoretical 5.91).

The structure of the compound obtained was confirmed by mass spectrometry, which was also used in the determination of the molecular weight of the compound: (MH)+ = 1049.

EXAMPLE 5

Preparation of 2,2'-butylidene-bis(2,4'-di-tert-butylphenyl)-N-dehydroabietyl-phosphorous amide Into a 250 ml double neck flask, equipped with a refrigerating device, in nitrogen atmosphere, are introduced in order: 100 ml of anhydrous toluene, 3.2 g (10 mmoles at 90%) of dehydroabietylamine, 1.5 ml (10.1 mmoles) of triethylamine, and 5.31 g (10 mmoles) of the 2,2'-butylidene-bis(2,4-di-tert-butylphenyl)phosphorous chloride prepared according to the procedure of Example A, but using 2,2'-butylidene-bis(2,4-di-tert-butylphenol) as the starting product instead of 2,2'-ethylidene-bis-(2,4-di-tertbutyl)phenol.

Operating as described in Example 1, 5.69 g (73% yield) of the desired product are obtained; the elemental analysis of said product is as follows:

C% 80.52 (theoretical 80.07); H% 10.31 (theoretical 10.08);

N% 1.69 (theoretical 1.79); P% 3.45 (theoretical 3.97).

The structure of the compound obtained was confirmed by way of mass spectrometry, which was also used in the determination of the molecular weight of the compound: (MH)+ = 780.

EXAMPLE 6

Preparation Of 2,2'-hexylidene-bis(2,4'-di-tert-butylphenyl)-N-dehydroabietyl-phosphorous amide Into a 250 ml double neck flask, equipped with a refrigerating device, in nitrogen atmosphere, are introduced in order: 100 ml of anhydrous toluene, 3.2 g (10 mmoles at 90%) of dehydroabietylamine, 2.25 ml (15.1 mmoles) of triethylamine, and 8.38 g (15 mmoles) of the 2,2'-hexylidene-bis (2,4-di-tert-butylphenyl ) phosphoric chloride prepared in Example A, but using 2,2'-hexylidene-bis (2,4-di -tert-butylphenol) as the starting product instead of 2,2'-ethylidene-bis-(2,4-di-tert-butyl)-phenol.

Operating as described in Example 1, 9.69 g (80% yield) of the desired product are obtained. The elemental analysis of said product is as follows:

C% 79.55 (theoretical 80.25); H% 9.89 (theoretical 10.23);

N% 1.63 (theoretical 1.73); P% 3.30 (theoretical 3.85).

The structure of the compound obtained was confirmed by mass spectrometry, which was also used in the determination of the molecular weight of the compound: (MH)+ = 808.

EXAMPLE 7

Preparation Of 2,2'-dodecylidene-bis(2,4'-di-tert-butylphenyl)-N-dehydroabietyl-phosphorous amide Into a 250 ml double neck flask, equipped with a refrigerating device, in nitrogen atmosphere, are introduced in order: 100 ml of anhydrous toluene, 1.84 g (5.8 mmoles at 90%) of dehydroabietylamine, 0.9 ml (6.5 moles) of triethylamine, and 3.76 g (5.8 mmoles) of 2,2'-dodecylidene-bis(2,4-di-tert-butylphenyl)phosphorous chloride prepared as in Example A, but using 2,2'-dodecylidene-bis(2,4-di-tert-butylphenol) as the starting product instead of 2,2'-ethylidene-bis-(2,4-di-tertbutyl)phenol.

Operating as described in Example 1, 4.6 g (89% yield) of the desired product are obtained. The elemental analysis of said product is as follows:

C% 80.76 (theoretical 79.34); H% 10.67 (theoretical 11.11);

N% 1.57 (theoretical 1.67); P% 3.09 (theoretical 3.47).

The structure of the compound obtained was confirmed by mass spectrometry, which was also used in the determination of the molecular weight of the compound: (MH)+ = 808.

EXAMPLE 8

Preparation Of 2,2'-dodecylidene-bis(2,4'-di-tert-butylphenyl)-N-cyclohexyl-phosphorous amide Into a 250 ml double neck flask, equipped with a refrigerating device, in nitrogen atmosphere, are introduced in order: 100 ml of anhydrous toluene, 3.7 ml (27 mmoles) of triethylamine, 2.5 ml (22 mmoles) of cyclohexylamine, and 14.3 g (22 mmoles) of 2,2'-dodecylidene-bis(2,4-di-tert-butylphenyl)-phosphorous chloride prepared as in Example A, but using 2,2'-dodecylidene-bis (2,4-di-tert-butylphenol) as the starting product instead of 2,2'-ethylidene-bis-(2,4-di-tert-butyl)phenol.

Operating as described in Example 1, 14.3 g (92% yield) of the desired product are obtained. The elemental analysis of said product is as follows:

C% 78.00 (theoretical 79.26); H% 10.90 (theoretical 10.86);

N% 1.85 (theoretical 1.98); P% 4.28 (theoretical 4.39).

The structure of the compound obtained was confirmed mass spectrometry, which was also used in the determination of the molecular weight of the compound: $(MH)^+ = 706$.

EXAMPLE 9

Preparation of 2,2'-butylidene-bis(2,4-di-tertbutylphenyl) -N-cyclohexyl-phosphorous amide Into a 250 ml double neck flask, equipped with a refrigerating device, in nitrogen atmosphere, are introduced in order: 100 ml of anhydrous toluene, 3.0 ml (21 mmoles) of triethylamine, 2.3 ml (20 mmoles) of cyclohexylamine, and 10.5 g (20 mmoles) of 2,2'-butylidene-bis (2,4-di-tert-butylphenyl)phosphorous chloride prepared as in Example A, but using 2,2'-butylidene-bis (2,4-di-tert-butylphenol) as the starting product instead of 2,2'-ethylidene-bis-(2,4-di -tert-butyl)phenol.

Operating as described in Example 1, 10.2 g (86% yield) of the desired product are obtained. The elemental analysis of said product is as follows:

C% 76.12 (theoretical 76.84); H% 9.95 (theoretical 10.18);

N% 2.16 (theoretical 2.36); P% 4.59 (theoretical 5.22).

The structure of the compound obtained was confirmed mass spectrometry, which was also used in the determination of the molecular weight of the compound: $(MH)^+ = 594$.

EXAMPLE 10

Preparation of 2,2'-hexylidene-bis(2,4'-di-tertbutylphenyl) -N-cyclohexyl-phosphorous amide Into a 250 ml double neck flask, equipped with a refrigerating device, in nitrogen atmosphere, are introduced in order: 100 ml of anhydrous toluene, 2 ml (14 mmoles) of triethylamine, 1.25 ml (11 mmoles) of cyclohexylamine, and 4.6 g (8.2 mmoles) of 2,2'-hexylidene-bis(2,4-di-tert -butylphenyl)phosphorous chloride prepared as in Example A, but using 2,2,-hexylidene-bis(2,4-di-tert-butylphenol) as the starting product instead of 2,2'-ethylidene-bis-(2,4-di -tert-butyl)phenol.

Operating as described in Example 1, 7.3 g (84% yield) of the desired product are obtained. The elemental analysis of said product is as follows:

C% 77.20 (theoretical 77.17); H% 10.57 (theoretical 10.03);

N% 2.03 (theoretical 2.25); P% 4.81 (theoretical 4.98).

The structure of the compound obtained was confirmed by mass spectrometry, which was also used in the determination of the molecular weight of the compound: $(MH)^+ = 622$.

EXAMPLE 11

This example illustrates the efficiency of the phosphorous amide compounds of the present invention, used in combination with phenolic antioxidants, in the thermal stabilization of the polypropylene.

100 parts by weight of isotactic polypropylene in powder form, type FLS20 available from HIMONT, are blended with 0.05 pans by weight of Irganox 1010 TM, a commercial product marketed by Ciba-Geigy to (pentaerythrityltetra[3(3,5-di-tert-butyl-4-hydroxyphenyl)propanoate]), and with 0.1 parts by weight of each of the compounds shown in Tables 1 and 2. To the blends thus obtained are added 70 parts by weight of acetone, and the mixture is agitated for 1 hour. After the solvent has been removed under reduced pressure, the polymer is blended with 0.1 parts by weight of calcium stearate.

The mixture is extruded five times in a single screw extruder at 100 rpm and a maximum temperature of 260° C. The Melt Flow Index of the polymer is measured (by way of ASTM D 1238, at a temperature of 230° C., and a load of 2.16 Kg), after the first, third, and fifth extrusion ($MFI_1$, $MFI_3$, $MFI_5$, respectively). The results obtained are shown in Table 1.

The purpose of process stabilizers is to reduce or eliminate the degradation of the polymer which takes place, for example, as a result of repeated extrusions at high temperatures. A measure of the degradation undergone by the polymer is the Melt Flow Index. In the case of polypropylene, the higher the degradation of the polymer, the higher the MFI of the polymer after a series of extrusions.

In analyzing the data in Tables 1 and 2, it can be seen that the phosphoric amides of the present invention are excellent as process stabilizers, and their performance is comparable, or in some cases even better, than that of phosphoric stabilizers commonly used for polypropylene.

TABLE 1

| STABILIZER | $MFI_1$ (g/10 min) | $MFI_3$ (g/10 min) | $MFI_5$ (g/10 min) |
|---|---|---|---|
| Control (1) | 4.0 | 6.6 | 14.3 |
| Compound Comp. Ex. 1 | 2.2 | 2.9 | 3.5 |
| Compound Comp. Ex. 2 | 2.2 | 2.9 | 3.7 |
| Compound Ex. 1 | 2.1 | 2.6 | 3.1 |
| Sandostab P-EPQ | 2.2 | 2.8 | 3.5 |

(1) Irganox 1010 was not added to the polypropylene.

TABLE 2

| STABILIZER | $MFI_1$ (g/10 min) | $MFI_3$ (g/10 min) | $MFI_5$ (g/10 min) |
|---|---|---|---|
| Control (1) | 4.0 | 6.6 | 14.3 |
| Compound Ex. 2 | 2.3 | 2.7 | 3.4 |
| Compound Ex. 3 | 2.2 | 2.6 | 3.0 |
| Compound Comp. Ex. 1 | 2.2 | 2.9 | 3.5 |
| Compound Comp. Ex. 2 | 2.2 | 2.9 | 3.7 |
| Compound Ex. 4 | 2.3 | 2.9 | 3.7 |
| Compound Ex. 5 | 2.2 | 2.8 | 3.8 |
| Compound Ex. 10 | 2.1 | 2.7 | 3.6 |
| Sandostab P-EPQ | 2.2 | 2.8 | 3.5 |

(1) Irganox 1010 was not added to the polypropylene.

EXAMPLE 12

This example illustrates the efficiency of the phosphorous amides of the present invention, used in combination with phenolic antioxidants, in the thermal stabilization of the polyethylene.

100 parts by weight of Eraclene TM HDG5515 P, a HDPE having a MFI of 11 g/10 min., are blended with 0.1 part by weight of the compound prepared in Example 9. To the mixture thus obtained are added 70 parts by weight of acetone, and the entire mixture is placed under agitation for 1 hour. After the solvent has been removed at reduced pressure, the polymer is blended with 0.05 parts by weight of calcium stearate.

The mixture is pelletized in nitrogen atmosphere at 230° C. The MFI of the polymer is 11.4. The mixture is extruded five times in a single-screw extruder at 100 rpm and a maximum temperature of 250° C. The MFI of the polymer is measured (at a temperature of 230° C. and with a load of 2.16 Kg, measured in g/10 min according to ASTM D 1238) after the first, third, and fifth extrusion ($MFI_1 = 11.5$, $MFI_3 = 11.6$, and $MFI_5 = 11.6$ respectively).

In the case of polyethylene a constant value of the polymer MFI after various extrusions at high temperatures is an indication of the stability of the polymer compared to the degradation, and, therefore, of the efficiency of the stabilizer.

EXAMPLE 13

Powder samples of the stabilizers of the present invention and other known phosphoric stabilizers were exposed to 28° C. at an 84% humidity. The water absorbed by the sample was determined by measuring the increase in weight after 4, 14, 28, 60 and 90 days. The percent variation of the acidity number of the samples compared with the initial acidity of the sample was also measured at the same time intervals. The acidity number is measured in mg of KOH/g of sample, and is determined by titration with $NaOCH_3$ of a solution of the sample in dimethylformamide.

The results of said measurements are shown in Tables 3 and 4.

By analyzing the data shown in Tables 3 and 4, it can be seen that the phosphorous amide of the present invention is not hygroscopic, and is hydrolysis stable under test conditions, while the P-EPQ and the phosphoramide of Comparative Example 1 (which differs from the compounds the present invention only in the A radical bonded to the nitrogen) are hygroscopic and hydrolizable under test conditions.

TABLE 3

| STABILIZER | Days of exposure | Weight variation | Acidity number var. |
|---|---|---|---|
| Compound Ex. 1 | 60 | 0 | 0 |
| Sandostab P-EPQ | 90 | 11 | +300 |

TABLE 3-continued

| STABILIZER | Days of exposure | Weight variation | Acidity number var. |
|---|---|---|---|
| Compound Comp. Ex. 1 | 14 | 0.85 | +100 |

TABLE 4

| STABILIZER | Days of exposure | Weight variation % | Acidity number var. % |
|---|---|---|---|
| Compound Ex. 2 | 90 | 0 | 0 |
| Compound Ex. 3 | 90 | 0 | 0 |
| Compound Ex. 4 | 60 | 0 | +2 |
| Compound Ex. 10 | 60 | 0 | +3 |
| Sandostab P-EPQ | 90 | 11 | +300 |
| Compound Comp. Ex. 1 | 14 | 0.85 | +100 |

EXAMPLE 14

100 parts by weight of the same polypropylene used in Example 10 are blended with 0.05 parts by weight of Irganox 1010, 0.05 parts by weight of GMS (glycerol monostearate), 0.05 parts by weight of calcium stearate, and 0.05 parts by weight of each of the stabilizers reported in Table 5.

The mixtures thus obtained are extruded at 230° C. in order to obtain a homogeneous distribution of the components, and then they are extruded three times in a twin-screw extruder at 100 rpm and at a final temperature of the cylinder of 280° C. The MFI is measured after each extrusion (at a 230° C. temperature and with a load of 2.16 Kg.) and the samples are then molded in order to measure the YI (Yellowing Index) according to ASTM D 1925-70 regulation. Said samples have a diameter of 50 mm and a thickness of 1 mm.

The data are reported in Table 5. From an evaluation of the data reported in Table 5, one can see that the use of the phosphorous amide of the present invention has some advantages over the use of the two comparative phosphoric compounds, both from the point of view of process stability and yellowing index.

TABLE 5

| STABILIZER | $MFI_1$ (g/10 min) | $MFI_2$ (g/10 min) | $MFI_3$ (g/10 min) | $YI_1$ | $YI_2$ | $YI_3$ |
|---|---|---|---|---|---|---|
| Compound Ex. 10 | 3.5 | 9.2 | 24.0 | 5.2 | 8.3 | 10.1 |
| Sandostab P-EPQ | 3.7 | 10.0 | 22.2 | 6.2 | 9.1 | 11.5 |
| Irgafos 168 | 4.7 | 15.1 | 25.1 | 6.95 | 9.44 | 12.2 |

We claim:

1. A phosphorous organic amide compound having the general formula:

where:

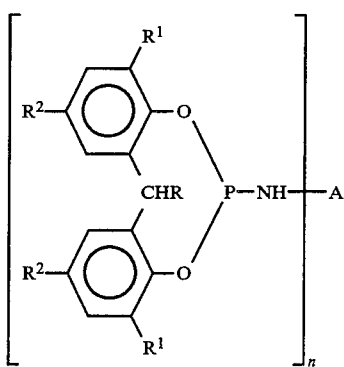

(I)

R is H or a $C_1$–$C_{18}$ alkyl radical, $R^1$ and $R^2$, are the same or different and are selected from linear or branched $C_1$–$C_{10}$ alkyl radicals, n is 1, and A is a radical of formula—$(CH_2)_m$—Cy, where Cy is selected from the group consisting or! abietyl, hydroabietyl, tetrahydroabietyl, dehydroabietyl, d- and l pimaryl and m is 0 or 1.

2. The phosphorous organic amide of claim 1, where R is H.

3. The phosphorous organic amide of claim 1, where R is a $C_1$–$C_{11}$ alkyl radical.

4. The phosphorous organic amide of claim 1, where $R^1$ and $R^2$ are the same or different and are selected from tert-butyl, isopropyl, methyl, and at least one of them is tert-butyl.

* * * * *

UNITED STATES PATENT AND TRADEMARK OFFICE
CERTIFICATE OF CORRECTION

PATENT NO. : 5,352,830
DATED : October 4, 1994
INVENTOR(S) : Marco Foa' et al

Page 1 of 2

It is certified that error appears in the above-indentified patent and that said Letters Patent is hereby corrected as shown below:

At col. 3, line 37, change "4" to -- $C_4$- --.

At col. 5, line 3, change "(II)+$PCl_3$+2B'!(III)+2B'.HCl" to --(II)+$PCl_3$+2B'$\rightarrow$(III)+2B'·HCl--.

At col. 5, line 14, change "Dr" to --or--.

At col. 5, line 21, change "B'eHCl," to --B'·HCl,--.

At col. 5, line 31, change "n(III)+$(H_2N)_n$A+nB"!(I)+nB".HCl" to --n(III)+$(H_2N)_n$A+nB"$\rightarrow$(I)+nB"·HCl--.

At col. 5, line 59, change "i00" to --100--.

At col. 6, line 39, change "Nl" to --Ni--.

UNITED STATES PATENT AND TRADEMARK OFFICE
CERTIFICATE OF CORRECTION

PATENT NO.   : 5,352,830

DATED        : October 4, 1994

INVENTOR(S)  : Marco Foa' et al

It is certified that error appears in the above-indentified patent and that said Letters Patent is hereby corrected as shown below:

At col. 6, line 60, change "moles" to --mmoles--.

At col. 7, line 22, change "moles" to --mmoles--.

At col. 9, line 2, change "field" to --yield--.

At col. 10, line 38, change "moles" to --mmoles--.

At col. 12, line 3, change "pans" to --parts--.

At col. 12, line 29, change "i" to --1--.

At col. 16, line 6, change "or!" to --of--.

Signed and Sealed this

Ninth Day of April, 1996

Attest:

BRUCE LEHMAN

*Attesting Officer*    *Commissioner of Patents and Trademarks*